United States Patent [19]
Volpin et al.

[11] Patent Number: 6,004,953
[45] Date of Patent: Dec. 21, 1999

[54] AGENT FOR SUPPRESSING TUMOR GROWTH

[75] Inventors: Mark Efimovich Volpin, deceased, late of Moscow, by Svetlana Mikhailovna Avaeva, administrator; Georgy Nikolaevich Vorozhtsov, Moscow; Nadezhda Jurievna Krainova, Moscow; Ilya Yakovlevich Levitin, Moscow; Jury Mikhailovich Luzhkov, Moscow; Evgeny Antonovich Lukiyanets, Moscow; Galina Konstantinovna Gerasimova, Moscow; Olga Stepanovna Zhukova, Moscow; Natalya Ivanovna Kazachkina, Moscow; Oleg Leonidovich Kalia, Moscow; Nikolaevna Novodarova Galina, deceased, late of Moscow, by Konstantin Igorevich Izvolsky, administrator; Elena Mikhailovna Treschalina, Moscow; Anatoly Borisovich Syrkin, Moscow; Valery Ivanovich Chissov, Moscow; Raisa Ivanovna Yakubovskaya, Moscow, all of Russian Federation

[73] Assignees: Institut Elementoorganicheskikh Soedineny Rossiiskoi Akademii Nauk; Gosudarsvenny Nauchy Tsentr Rossiiskoi Federatsii "Niopik"; Onkologichesky Nauchy Tsentr Rossiiskoi Akademii Nauk; Moskovsky Naucho-Issledovatelsky Onkologichesky Institut, all of Moscow, Russian Federation

[21] Appl. No.: 08/809,483

[22] PCT Filed: Mar. 18, 1996

[86] PCT No.: PCT/RU96/00060

§ 371 Date: May 27, 1997

§ 102(e) Date: May 27, 1997

[87] PCT Pub. No.: WO97/03666

PCT Pub. Date: Feb. 6, 1997

[30] Foreign Application Priority Data

Jul. 17, 1995 [RU] Russian Federation ............. 95112240

[51] Int. Cl.$^6$ .................................................. A61K 31/555
[52] U.S. Cl. ............................................................ 514/185
[58] Field of Search ............................................. 514/185

[56] References Cited

U.S. PATENT DOCUMENTS 4,393,071  7/1983  Fujii et al. ................................ 424/274
5,358,940  10/1994  Capraro et al. ............................ 514/63

FOREIGN PATENT DOCUMENTS 0484027  5/1992  European Pat. Off. .
WO95/05818  3/1995  WIPO .

OTHER PUBLICATIONS

E. Kimoto, Cancer Research 43, pp. 824–828, Feb. 1983, "Enhance-ment of Antitumor Activity of Ascorbate against Ehrlich . . . ".

(List continued on next page.)

*Primary Examiner*—Russell Travers
*Attorney, Agent, or Firm*—Jacobson, Price, Holman & Stern, PLLC

[57] ABSTRACT

The invention relates to the field of biology and medicine, in particular to suppression of the growth of malignant tumors.

The object of the present invention is to find more effective and less toxic drugs for suppression of tumor growth.

The essence of the proposed invention is that in order to suppress tumor growth, a drug consisting of a biogenic reductant and a complex of cobalt or iron with substituted phthalocyanines (I) or naphthalocyanines (II) is used.

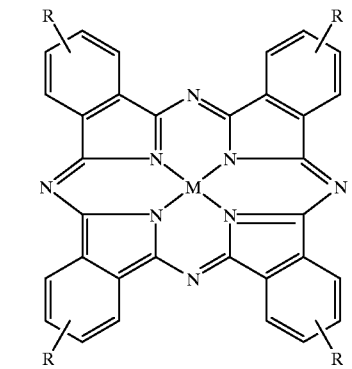

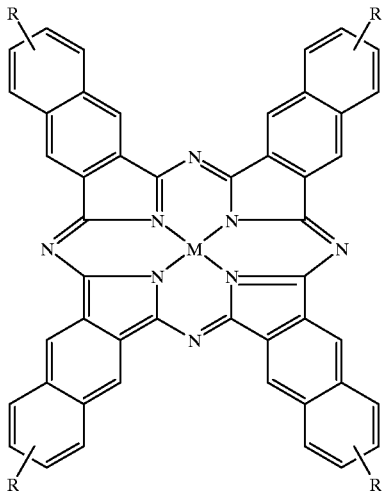

where R=COONa, $SO_3Na$, $CH_2C_5H_5N^{\oplus}Cl^-$, $CH_2(NH_2)_2S^{\oplus}CCl^-$.

Use of the proposed drug makes it possible to suppress effectively the growth of a wide range of malignant tumors, in particular to achieve the suppression of proliferation of cancer cells (in vitro), inhibition of the growth of tumors in mice (in vivo) and a substantial increase in their life-span, including that obtained in comparison with use of the prototype.

9 Claims, No Drawings

OTHER PUBLICATIONS

Science, vol. 262, pp. 32–33, Oct. 1993, "Hope for a Magic Bullet That Moves at the Speed of Light".

Aust, Journal of Free Radicals, vol. 1, pp. 3–25, 1985, "Role of Metals in Oxygen Radical Reactions".

Rose, Cancer Treatment Reports vol. 66, No. 1, Jan. 1982, "Anti–tumor Activity and Toxicity of Cisplatin Analogs".

AGENT FOR SUPPRESSING TUMOR GROWTH

The invention relates to the field of biology and medicine, in particular to suppression of the growth of malignant tumors.

The following drugs are known for suppression of tumor growth.

1. Cis-dichlorodiaminoplatinum. Having a wide range of action, it is used for treatment of solid tumors of various localization [1,2], but exhibits high nephrotoxicity [3].

2. Photodynamic therapy of tumors, in which photosensitizers—free tetrapyrrolic macrocyclic ligands or their complexes with metals, e.g. aluminum complex of sulfonated phthalocyanine Al[Pc(SO$_3$H)$_4$]—are used. Their use is only possible in the case of surface located tumors, more exactly—accessible for a laser probe [4].

3. A drug consisting of a complex of copper (II) with glycylglycylhistidine tripeptide ([Cu(GGH)]Cl) and sodium salt of ascorbic acid in a ratio of 1:10 is the drug most similar to that proposed; it causes an increase in the life-span (ILS) of mice with Ehrlich ascitic carcinoma [5].

Drawbacks of the prototype are low effectiveness related to the low selectivity of that complex in respect of tumors and its instability in physiological conditions, and a high toxicity due to the products of decomposition of the complex.

The object of the present invention is to find more effective and less toxic drugs for suppression of tumor growth.

The essence of the proposed invention is that a drug consisting of a biogenic reductant and a complex of cobalt or iron with substituted phthalocyanines (I) or naphthalocyanines (II) is used to suppress tumor growth.

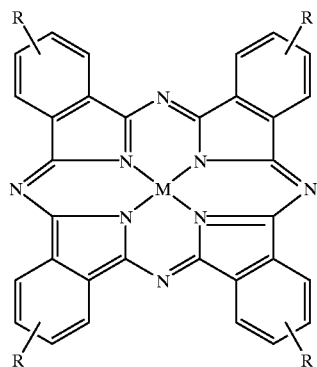

I

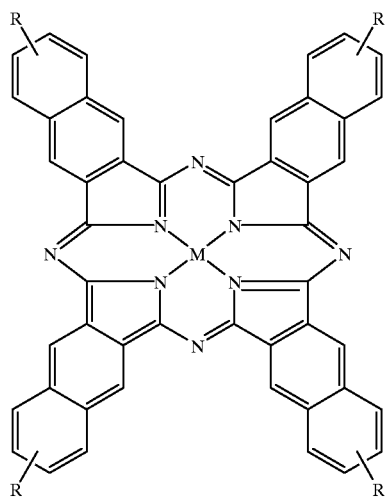

II where R=COONa, SO$_3$Na, CH$_2$C$_5$H$_5$N$^\oplus$Cl$^-$, CH$_2$(NH$_2$)$_2$S$^\oplus$CCl$^-$.

The scientific foundation for the invention is literary data on the selective accumulation of tetrapyrrolic macrocyclic compounds and their complexes with metals in tumorous tissues [4, 6] and the facts that we have established which show the high catalytic activity of phthalocyanine complexes of cobalt and iron in model chemical systems, in particular:

1) they are homogenic catalysts of the autooxidation row of biogenic reductants and analogues thereof, e.g. ascorbic acid, ubiquinone and cysteine;
2) the (intermediate) formation of active forms of oxygen—the anion-radical of superoxide, hydrogen peroxide and a hydroxyl radical, the cytostatic and other biological activity of which is well known—takes place in this reaction [7];
3) in the conditions of this reaction, the proposed complexes cause an oxidative degradation of nucleic acids.

METHODS AND RESULTS OF TESTS

Tests of the proposed drug for cytotoxic and antitumor activity were carried out on cultures of tumor cells (in vitro) and on mice with regrafted tumors (in vivo).

DETERMINATION OF THE ACTIVITY OF THE DRUGS ON CULTURES OF TUMOR CELLS (IN VITRO)

Method 1

The method of evaluation of the cytostatic effect of a combination of phythalocyanines with ascorbic acid in a system in vitro was developed on a culture of tumor cells of human testicular carcinoma (Cao V line).

The culture of cells was grown in a monolayer in medium 199 comprising a 10% solution of an embryonic calf serum.

At the beginning of the experiment the cells were inoculated at a density of 100000/ml in a total volume of 2 ml and incubated at 37° C. for 24 hours. Then the testing was carried out in the following variants:

1. Control

The growth medium for the samples was replaced with a fresh intact nutrient medium and incubated for 48 hours, then $^3$H-thymidine ($^3$H-T) in a final concentration of 1 $\mu$Curie/ml was introduced into the medium of the samples, it was washed with a Hank's solution, a 2.5% solution of perchloric acid, and the acid-insoluble fraction was hydrolyzed in 5 ml of 5% perchloric acid. The hydrolyzates in a volume of 100 $\mu$l were transferred into flasks with a scintillation fluid SF-8 and the level of radioactivity in the samples was registered on a RackBeta (Sweden) fluid scintillation counter. The average values of the level of radioactivity were calculated.

2. In order to evaluate the effect of ascorbic acid on the growth of cells of the Cao V line, the growth medium of the samples was replaced with a fresh medium, comprising ascorbic acid in a concentration of $1 \times 10^{-4}$ M, incubated for 4 hours, and then the sample was processed according to the method described in para 1.

3. In order to evaluate the effect of phthalocyanine metal complexes on the growth of cells of the Cao V line, the growth medium of the samples was replaced with a fresh medium, comprising complexes in a predetermined concentration, the method described in para 1 was followed.

4. In order to evaluate the cytostatic effect of the combination of phthalocyanine and ascorbic acid, ascorbic acid was added into the growth medium comprising the complex in a ratio of concentration equal to 1:10, and the method described in para 1 was followed.

The suppression of the $^3$H-T inclusion in the test samples was calculated according to the equation $$\left(1 - \frac{\text{average value of decomposition/min/test samples}}{\text{average value of decomposition/min/control samples}}\right) \times 100\%$$

Statistic processing of the results was carried out using the method of sample analysis.

Method 2

Determination of the cytostatic activity of the drugs being tested was carried out using a biotest based on inhibiting the proliferation of a regrafted culture of cells of human lung adenocarcinoma A-549, due to the action of cytotoxic agents.

In order to cultivate cells of the A-549 line, the Eagle medium was used with the addition of 100 $\mu$g/ml of heptamycin and a 10% solution of embryonic calf serum, preliminarily inactivated by heating. Cultivation of the cells was carried out under standard conditions: at 37° C. in a humid atmosphere, comprising 5% carbon dioxide.

When a cytostatic biotest was being set up, 100 $\mu$l of a suspension of cells of the A-549 line at a concentration of $7.5 \times 10^4$ cells/ml were placed in each of the craters of a flat 96-crater microboard ("Sarstedt," USA) with addition of the drugs being tested in a volume of 100 $\mu$l/crater at the beginning of the phase of logarithmic growth.

The cytostatic activity of the drugs being tested was evaluated by the colorimetric method, based on the capability of mitochondrial dehydrogenases of live test-cells of restoring exogenetically introduced soluble 3-(4,5-dimethyl-2-thiazolyl)-2,5-diphenyl-2H-tetrazole bromide (MTT, "Sigma Chemical Co.," USA) into an insoluble crystalline formazan. Wherein, 20 $\mu$l of a solution of MTT at a concentration of 5 mg/ml were put into each crater of the 96-crater microboard, after which the cell cultures were centrifuged, the whole volume of the culture medium was removed from the craters. For solubilization of the colored reaction products (crystals of formazan), 150 $\mu$l of dimethylsulfoxide ("Sigma") were introduced into each crater of the microboard and the microboard was incubated at room temperature and continuously shaken. The results were registered upon absorption at a wavelength of 550 nm on the minireader "Dynatech" (FRG).

The level of inhibition of proliferation of the cell cultures by the drugs being tested for cytostatic activity was calculated according to the equation:

$$IP(\%) = 100\% - \frac{P_t}{P_c} \times 100\%,$$

where:
IP is the level of inhibition of the proliferation;
$P_t$ is the level of proliferation in the test (with the drugs): absorption of the dye in test samples;
$P_c$ is the level of proliferation in the control (without the drugs): absorption of the dye in test samples.

Data are presented in Table 1 on the absence of cytotoxic activity of ascorbic acid (AH$_2$) by itself and of phthalocyanine complexes relative to cells of the Cao V and MCF-7 lines at a predetermined criterion of activity CE$_{50}$ equal to $10^{-4}$ M for a 48-hour period of incubation.

TABLE 1

Antiproliferation activity of components of the claimed drug (phthalocyanine and naphthalocyanine complexes of metals and ascorbic acid) relative to tumor cells of a human in vitro

| | CE$_{50}$, M | |
|---|---|---|
| Content | Human testicular carcinoma CaoV* | Breast adenocarcinoma MCP-7 line[ |
| Co[Pc(SO$_3$Na)$_2$] | 2.5 × 10$^{-4}$ | |
| Fe[Pc(SO$_3$Na)$_2$] | 2 × 10$^{-4}$ | |
| Fe[Pc(COONa)$_8$] | 0.5 × 10$^{-4}$ | |
| Co[Pc(CH$_2$C$_5$H$_5$N$^\oplus$)$_6$]Cl$^-_6$ | 5 × 10$^{-4}$ | 1 × 10$^{-4}$ |
| Co[Pc(SO$_3$H)$_2$] | 5 × 10$^{-4}$ | 1 × 10$^{-4}$ |
| Co[Pc(CH$_3$(NH$_2$)$_2$S$^\oplus$CCl$^-$)$_8$] | 2.5 × 10$^{-4}$ | |
| Co[Nc(CH$_2$C$_5$H$_5$N$^\oplus$)$_2$]Cl$^-_2$ | 1 × 10$^{-4}$ | |
| Co[Pc(COONa)$_8$] | 5 × 10$^{-4}$ | 1 × 10$^{-4}$ |
| AH$_2$ | >1 × 10$^{-3}$ | >1 × 10$^{-3}$ |

*AH$_2$ - ascorbic acid.

The compound was considered to be active if CE$_{50}$ [the concentration at which a 50% suppression of inclusions $^3$H-T in the cells (see method 1)] was $1 \times 10^{-4}$M under these conditions of the experiment. As is evident from the presented results, the complex Co[Nc(CH$_2$C$_5$H$_5$N$^\oplus$)$_2$]Cl$^-_2$ and the complex Fe[Pc(COONa)$_8$] had limited activity, all the other complexes and AH$_2$ were inactive.

Data are grouped in Table 2 which were obtained during a study of the inhibition of the proliferation of tumor cells in vitro when phthalocyanines and ascorbic acid were used together in noncytotoxic concentrations.

TABLE 2

Inhibition of the proliferation of tumor cells in the presence of phthalocyanine and naphthalocyanine complexes of metals and ascorbic acid when simultaneously administered into a culture of cells

| | Inhibition of proliferation (%) | | |
|---|---|---|---|
| | Human testicular carcinoma CaoV* | Breast adeno-carcinoma, MCF-7* line | Human lung carcinoma A-549** |
| $Co[Pc(SO_3Na)_2]$ | 0 | | 0 |
| $Co[Pc(SO_3Na)_2] + AH_2$ | 52 | | 83 |
| $Fc[Pc(SO_3Na)_2]$ | 0 | | |
| $Fe[Pc(SO_3Na)_2 + AH_2$ | 12 | | |
| $Fe[Pc(COONa)_8]$ | 50 | | |
| $Fe[Pc(COONa)_8] + AH_2$ | 51 | | |
| $Co[Pc(CH_2C_5H_5N^{\oplus})_6Cl^-_6]$ | 0 | 0 | 0 |
| $Co[Pc(CH_2C_5H_5N^{\oplus})_6Cl^-_6] + AH_2$ | 74 | 50 | 55 |
| $Co[Pc(SO_3H)_2]$ | 0 | 0 | |
| $Co[Pc(SO_3H)_2] + AH_2$ | 76 | 30 | |
| $Co[Pc(CH_2(NH_2)_2S^{\oplus}CCl^-)_8]$ | 0 | | |
| $Co[Pc(CH_2(NH_2)_2S^{\oplus}CCl^-)_8] + AH_2$ | 64 | | |
| $Co[Nc(CH_2C_5H_5N^{\oplus})_2]Cl^-_2$ | 0 | | |
| $Co[Nc(CH_2C_5H_5N^{\oplus})_2]Cl^-_2 + AH_2$ | 64 | | |
| $Co[Pc(COONa)_8]$ | 0 | 0 | |
| $Co[Pc(COONa)_8] + AH_2$ | 99.5 | 86 | |

\* - method 1, [complex] = $5 \cdot 10^{-5}$M, [$AH_2$] = $1 \cdot 10^{-4}$M.
\*\* - method 2, [complex] = 100 µg/ml, [$AH_2$] = 227 µg/ml

DETERMINATION OF ANTITUMOR ACTIVITY OF THE DRUGS ON MICE WITH REGRAFTED TUMORS (IN VIVO)

Tests were carried out on tumor strains: Ehrlich ascitic carcinoma (example 1), ascitic hepatoma 22 (examples 2, 3), solid breast adenocarcinoma Ca-755 (example 4).

The complexes are dissolved in a sterile physiological solution until a concentration of from 0.005 to 1% is obtained. Ascorbic acid is dissolved in sterile distilled water or an isotonic solution of sodium chloride to a concentration of from 0.011 to 2.2%. The complexes and ascorbic acid are administered intraperitoneally, intrapleurally, intravenously or into the tumor itself.

EXAMPLE 1

A tumor, an Ehrlich ascitic carcinoma, was grafted into mice intrapleurally. The tests were carried out in a manner similar to that of Example 2.

Mice of the control group without treatment died on the 9th–15th day with development of tumorous pleurisy.

Mice, who had received treatment with a complex of $Co[Pc(COONa)_8]$ in a single dose of 75 mg/kg with subsequent administration of 165 mg/kg of ascorbic acid, lived for 18–40 days. Death from toxicity was not observed (Table 3).

EXAMPLE 2

A tumor, ascitic hepatoma 22, was grafted intraperitoneally, the grafting dose was $10^6$ cells per mouse. Mice of both sexes were used. The weight of each mouse was at least 18 g. Treatment was begun 48 hours after the tumor was grafted. Mice of the control group without treatment lived 19.3+1.7 days and died with expressed ascites. In the group of mice receiving treatment with a complex of $Co[Pc(COONa)_8]$ in a single dose of 100 mg/kg with subsequent administration of ascorbic acid (a course dose of 550 mg/kg), one mouse died on the 19th day with ascites, the remaining 8 of the 9 mice lived without symptoms of tumor for more than 70 days. Death from toxicity was not observed (Table 3).

EXAMPLE 3

Tests were carried out in a manner similar to that in example 1, but the tumor, ascitic hepatoma 22, was grafted to the mice intrapleurally.

Mice of the control group without treatment lived 5.7+1.6 days and died with exudation of the pleural cavity in a volume of about 2.0 ml.

In the group of mice who received treatment with a complex of $Co[Pc(COONa)_8]$ in a single dose of 75 mg/kg with subsequent administration of 165 mg/kg of ascorbic acid, the mice lived more than 70 days without symptoms of a tumor. Death from toxicity was not observed (Table 3).

TABLE 3

Effect of complex $Co[Pc(COONa)_8]$ and ascorbic acid ($AH_2$) on the life-span of mice with grafted tumors, as compared with the prototype

| | Tumor strain | | | |
|---|---|---|---|---|
| | Ehrlich carcinoma | | Hepatoma 22 | |
| Substance | ALS, % | Recovery, % | ALS, % | Recovery, % |
| $Co[Pc(COONa)_8] + AH_2$ | 296 | 0 | 370 | 70 |
| [Cu(GGH)]Cl(prototype [5]) | 60 | 0 | | |

EXAMPLE 4

Breast adenocarcinoma Ca-755 was grafted into the mice using 50 mg of tumorous tissue. Treatment was begun 48 hours or on the 9th day after the tumor was grafted. The complexes and ascorbic acid were administered in several ways: intravenously, intraperitoneally, intratumorously (Table 4).

The results obtained with mice having tumors were evaluated by means of generally accepted indexes of antitumor activity, with mice who were not given antitumor therapy being used for control.

Calculation of the increase of life-span was made using the equation:

$$ALS = \frac{L_{test} - L_{control}}{L_{control}} \times 100\%,$$

where

L is the life-span in days.

Inhibition of tumor growth was calculated for solid tumors using the equation:

$$TGI = \frac{V_{average\ control} - V_{average\ test}}{V_{average\ control}} \times 100\%,$$

where $V_{average}$ is the average volume of the tumor, calculated as the product of three measurements and expressed in cubic cm.

Regression of the tumor was determined from a developed solid adenocarcinoma Ca-755, the percentage of regression was calculated by the equation:

$$R = \frac{V_o - V_n}{V_o} \times 100\%,$$

where
R is the percentage of regression,
$V_o$ is the initial average volume of a tumor,
$V_n$ is the average volume of a tumor after treatment for "n" days.

TABLE 4

Inhibition of the growth of a solid breast adenocarcinoma Ca-755 after administration of phthalocyannie complexes of colbalt and ascorbic acid ($AH_2$)

| Complex | Dose (mg/kg) | TGI*, % |
|---|---|---|
| Co[Pc(CH$_2$C$_5$H$_5$N$^\oplus$)$_6$]Cl$^-$$_6$ | 25 | 58 |
| AH$_2$ | 27.5 | 38 |
| CO[Pc(CH$_2$C$_5$H$_5$$^\oplus$)$_6$]Cl$^-$$_6$ + AH$_2$ | 25 + 27.5 | 91 |
| Co[Pc(SO$_3$Na)$_2$] | 25 | 68 |
| AH$_2$ | 56.75 | 66 |
| Co[Pc(SO$_3$Na)$_2$]+ AH$_2$ | 25 + 56.75 | 88 |
| Co[Pc(COONa)$_8$] | 10 | 44 |
| AH$_2$ | 22 | 33 |
| CO[PC(COONa)$_8$] + AH$_2$ | 10 + 22 | 61 |

\* - data in respect of Co complexes Co[Pc(CH$_2$C$_5$H$_5$N$^\oplus$)$_6$] and Co[Pc(SO$_3$Na$_2$] and presented for the 14th day, data in respect of the complex Co[Pc(COONa)$_8$] are presented for the 16h day after transplantation of the tumors.

Thus, use of the proposed drug makes it possible to suppress effectively the growth of a wide range of malignant tumors, in particular to achieve the suppression of proliferation of cancer cells (in vitro) and inhibition of the growth of tumors in mice (in vivo) and substantially increase their life-span, including that obtained in comparison by use of the prototype.

LITERATURE

1. Rose W. C. et al., Cancer Treatment Rep., 1982, 66, 135–146.

2. Gorbunova V. A., Voproxy Onkology, 1989, 35, 325–331.

3. Belgorodsky V. V. et al., Voproxy Onkology, 1975, 21, 95–105.

4. Mironov A. F., "Photosensitizers on the base of porphyrins and related compounds for photodynamic therapy of cancer" in book "Itogi nauki i tekhniki," VINITI, Moscow, 1990, 3, 5–62.

5. Kimoto E., Tanaka H., Gyutoku J., Morishige F., Pauling L., Cancer Research, 1983, 43, 824–828.

6. Amato I., Science, 1993, 262, 32–33.

7. Aust S. D., Morehouse L. A. and Thomas C. E., J. of Free Radicals in Biology & Medicine, 1985, 1, 3–25.

It is claimed:

1. A composition for tumor growth suppression, comprising a synergistic complex of cobalt or iron with substituted phthalocyanines or naphthalocyanines of the structural formula I or II:

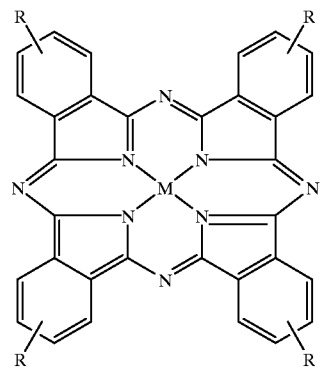

I

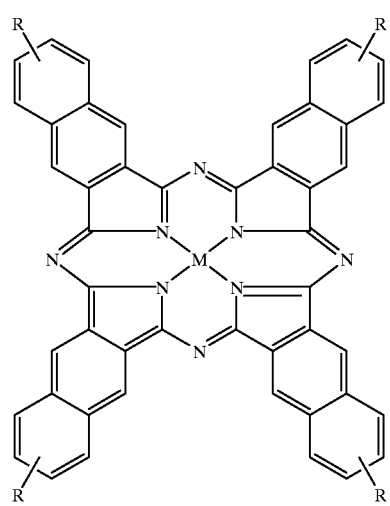

II wherein M is selected from the group consisting of Co and Fe; and R is selected from the group consisting COONa, SO$_3$Na, CH$_2$C$_5$H$_5$N$^\oplus$Cl—, CH$_2$(NH$_2$) $_2$S$^\oplus$CCl—; combined with a synergistic amount of ascorbic acid in a ratio of from 1:5 to 1:50.

2. The composition of claim 1, wherein M is Co.

3. The composition of claim 1, wherein M is Fe.

4. The composition of claim 1, wherein R is COONa.

5. The composition of claim 1, wherein R is SO$_3$Na.

6. The composition of claim 1, wherein R is CH$_2$C$_5$H$_5$N$^+$Cl$^-$.

7. The composition of claim 1, wherein R is CH$_2$(NH$_2$) $_2$S$^+$CCl$^-$.

8. The composition of claim 1, wherein the biogenic reductant is selected from the group consisting of ascorbic acid, ubiquinone and cysteine.

9. A method for the catalytic treatment of cancer comprising:
administering an effective amount of a composition of claim 1 to a mammal; and
suppressing tumor growth in said mammal by catalytic action of said composition.

\* \* \* \* \*